(12) United States Patent
Odry et al.

(10) Patent No.: US 8,019,140 B2
(45) Date of Patent: Sep. 13, 2011

(54) SYSTEM AND METHOD FOR DETERMINING A SIZE OF AN AIRWAY LUMEN AND A THICKNESS OF AN AIRWAY WALL

(75) Inventors: Benjamin Odry, West New York, NJ (US); Atilla Peter Kiraly, Plainsboro, NJ (US); Carol L. Novak, Newtown, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1426 days.

(21) Appl. No.: 11/465,516

(22) Filed: Aug. 18, 2006

(65) Prior Publication Data
US 2007/0049840 A1 Mar. 1, 2007

Related U.S. Application Data

(60) Provisional application No. 60/713,025, filed on Aug. 31, 2005.

(51) Int. Cl.
G06K 9/00 (2006.01)
A61B 5/103 (2006.01)
A61B 5/117 (2006.01)

(52) U.S. Cl. ............... 382/131; 382/128; 600/587
(58) Field of Classification Search ............ 600/479, 600/481, 587, 593; 382/128, 131
See application file for complete search history.

(56) References Cited

U.S. PATENT DOCUMENTS 6,301,498 B1 * 10/2001 Greenberg et al. ........... 600/425
6,829,379 B1 * 12/2004 Knoplioch et al. ........... 382/131
7,149,333 B2 * 12/2006 Pieper et al. ................. 382/128
7,333,648 B2 * 2/2008 Edic et al. .................... 382/131
7,970,193 B2 * 6/2011 Rouet et al. .................. 382/131

OTHER PUBLICATIONS

R. Wiemker, T. Blaffert, T. Bülow, S. Renisch, C. Lorenz, "Automated Assessment of bronchial lumen, wall thickness, and bronchoarterial diameter ratio of the tracheobronchial tree using high resolution CT", *CARS 2004*: 967-972.
K Li, X Wu, D. Z. Chen, M. Sonka, "Efficient Optimal Surface Detection: Theory, Implementation and Experimental Validation," SPIE Medical Imaging 2004: SPIE Proceedings vol. 5370, Feb. 2004.
A. P. Kiraly, J. M. Reinhardt, E. A. Hoffman, G. McLennan, W. E. Higgins, "Virtual Bronchoscopy for Quantitative Airway Analysis" *SPIE Medical Imaging 2005: Physiology, Function, and Structure from Medical Images*, A. Amini and A. Manduca, eds, SPIE Proceedings vol. 5746, Feb. 2005.
A. P. Kiraly, J. P. Helferty, E. A. Hoffman, G. McLennan, W. E. Higgins, "Three-Dimensional Path Planning for Virtual Bronchoscopy" IEEE Transactions in Medical Imaging, pp. 1365-1379, vol. 23, No. 11, Nov. 2004.

* cited by examiner

*Primary Examiner* — Max Hindenburg
*Assistant Examiner* — Adam Eiseman

(57) ABSTRACT

A method for determining a size of an airway lumen and a thickness of an airway wall includes: computing a centerline of an airway; computing a three-dimensional (3D) gradient of a volume of the airway within a first threshold; positioning a tube along the centerline; iteratively expanding the tube by increasing its radius until the radius of the tube reaches the first threshold; determining inner and outer radii of the tube by checking the 3D gradient computed along an x-axis and a y-axis of the tube at a boundary of the tube at each iteration; and fitting the tube to the airway by using the determined inner and outer radii, wherein the inner radius of the fit tube is half a diameter of the airway lumen and the outer radius of the fit tube minus the inner radius of the fit tube is a thickness of the airway wall.

18 Claims, 6 Drawing Sheets

SYSTEM AND METHOD FOR DETERMINING A SIZE OF AN AIRWAY LUMEN AND A THICKNESS OF AN AIRWAY WALL

CROSS-REFERENCE TO RELATED APPLICATION

This application claims the benefit of U.S. Provisional Application No. 60/713,025, filed Aug. 31, 2005, a copy of which is herein incorporated by reference.

BACKGROUND OF THE INVENTION

1. Technical Field

The present invention relates to medical image processing, and more particularly, to a system and method for determining a size of an airway lumen and a thickness of an airway wall.

2. Discussion of the Related Art

Pulmonary diseases such as bronchiectasis, asthma and emphysema are characterized by abnormalities in airway dimensions, including airway wall thickness and lumen diameter. Multi-slice computed tomography (MSCT) has become one of the primary means to depict these abnormalities as the availability of high-resolution near-isotropic data makes it possible to evaluate airways at angles that are oblique to a scanning plane. However, clinical evaluation of the airways is generally limited to visual inspection.

Recently, automated methods have been proposed that are based on the extraction of a bronchial tree model and its segmentation. One method described in A. P. Kiraly, J. M. Reinhardt, E. A. Hoffman, G. McLennan, W. E. Higgins, "Virtual Bronchoscopy for Quantitative Airway Analysis" SPIE Medical Imaging, 2005: Physiology, Function, and Structure from Medical Images, A. Amini and A. Manduca, eds, SPIE Proceedings vol. 5746, February, 2005, relies on a full-width half-max method to determine the radii of the inner and outer walls. In another method described in R. Wiemker, T. Blaffert, T. Bulow, S. Renisch, C. Lorenz, "Automated Assessment of bronchial lumen, wall thickness, and bronchoarterial tree using high resolution CT", CARS 2004: 967-972, measurements based on radial derivatives are used. However, since no correlation is enforced between individual radius measurements with these methods, there exists the potential for errors near bifurcations and at walls with nearby blood vessels. For example, a reading of 1 mm can be obtained in one direction while a reading of 2 mm can be obtained in a nearby direction.

To reduce the possibility of errors near bifurcations and at walls with nearby blood vessels, a correlation enforcement method was introduced in K. Li, X. Wu, D. Z. Chen, M. Sonka, "Efficient Optimal Surface Detection: Theory, Implementation and Experimental Validation," SPIE Medical Imaging 2004: SPE Proceedings vol. 5370, February 2004. In this method, a plane is fit to reformatted data and an optimal surface is determined. However, here, only the lumen is measured.

SUMMARY OF THE INVENTION

In an exemplary embodiment of the present invention, a method for determining a size of an airway lumen and a thickness of an airway wall, comprises: computing a centerline of an airway; computing a three-dimensional (3D) gradient of a volume of the airway within a first threshold; positioning a tube along the centerline; iteratively expanding the tube by increasing its radius until the radius of the tube reaches the first threshold; determining inner and outer radii of the tube by checking the 3D gradient computed along an x-axis and a y-axis of the tube at a boundary of the tube at each iteration; and fitting the tube to the airway by using the determined inner and outer radii, wherein the inner radius of the fit tube is half a diameter of the airway lumen and the outer radius of the fit tube minus the inner radius of the fit tube is a thickness of the airway wall.

The first threshold is a maximum size of the tube. The method further comprises increasing the radius of the tube by a quarter of an isotropic voxel at each iteration. The method further comprises separating the tube into right and left sections for the 3D gradient computed along the x-axis of the tube and into top and bottom sections for the 3D gradient computed along the y-axis of the tube.

Determining inner and outer radii of the tube comprises: computing a mean gradient curve of the right, left, top and bottom sections; and performing a peak analysis of the mean gradient curves. A maximum peak of the mean gradient curves corresponds to an inner radius of the tube and a minimum peak of the mean gradient curves corresponds to an outer radius of the tube.

Fitting the tube to the airway by using the determined inner and outer radii comprises: validating, as part of the airway, points from the inner and outer diameters that are common to the 3D gradients computed along the x and y-axes of the tube; computing a second threshold corresponding to a third of a maximum value of the 3D gradients computed along the x and y-axes of the tube for inner and outer diameter points from only one of the 3D gradients computed along the x and y-axes of the tube; discarding points from only one of the 3D gradients computed along the x and y-axes of the tube when they are below the second threshold; and validating points from only one of the 3D gradients computed along the x and y-axes of the tube when they are above the second threshold.

The method further comprises filling holes between neighboring points that have been validated in the fit airway by placing farthest distance value points from the centerline between the neighboring points. The method further comprises acquiring an image of a chest including the airway by using computed tomography or magnetic resonance imaging. The airway is a trachea or a bronchi.

In an exemplary embodiment of the present invention, a system for determining a size of an airway lumen and a thickness of an airway wall, comprises: a memory device for storing a program; a processor in communication with the memory device, the processor operative with the program to: compute a centerline of an airway; compute a 3D gradient of a volume of the airway within a first threshold; position a tube along the centerline; iteratively expand the tube by increasing its radius until the radius of the tube reaches the first threshold; determine inner and outer radii of the tube by checking the 3D gradient computed along an x-axis and a y-axis of the tube at a boundary of the tube at each iteration; and fit the tube to the airway by using the determined inner and outer radii, wherein the inner radius of the fit tube is half a diameter of the airway lumen and the outer radius of the fit tube minus the inner radius of the fit tube is a thickness of the airway wall.

The first threshold is a maximum size of the tube. The processor is further operative with the program to increase the radius of the tube by a quarter of an isotropic voxel at each iteration. The processor is further operative with the program to separate the tube into right and left sections for the 3D gradient computed along the x-axis of the tube and into top and bottom sections for the 3D gradient computed along the y-axis of the tube.

When determining inner and outer radii of the tube the processor is further operative with the program to: compute a mean gradient curve of the right, left, top and bottom sections; and perform a peak analysis of the mean gradient curves. A maximum peak of the mean gradient curves corresponds to an inner radius of the tube and a minimum peak of the mean gradient curves corresponds to an outer radius of the tube.

When fitting the tube to the airway by using the determined inner and outer radii the processor is further operative with the program to: validate, as part of the airway, points from the inner and outer diameters that are common to the 3D gradients computed along the x and y-axes of the tube; compute a second threshold corresponding to a third of a maximum value of the 3D gradients computed along the x and y-axes of the tube for inner and outer diameter points from only one of the 3D gradients computed along the x and y-axes of the tube; discard points from only one of the 3D gradients computed along the x and y-axes of the tube when they are below the second threshold; and validate points from only one of the 3D gradients computed along the x and y-axes of the tube when they are above the second threshold.

The processor is further operative with the program to fill holes between neighboring points that have been validated in the fit airway by placing farthest distance value points from the centerline between the neighboring points. The processor is further operative with the program to acquire an image of a chest including the airway by using a computed tomography or magnetic resonance imaging device. The airway is a trachea or a bronchi.

In an exemplary embodiment of the present invention, a method for refining a segmentation of an airway in a chest of a patient, comprises acquiring an image of the chest by using computed tomography or magnetic resonance imaging; segmenting a lumen of the airway by growing a first tube positioned along a centerline of the airway to determine inner radii of the airway by checking a 3D gradient computed along an x-axis and a y-axis of the first tube at a boundary of the first tube; fitting the first tube to the airway by using the determined inner radii, wherein the inner radius of the tube is half a diameter of the airway lumen; segmenting a wall of the airway by growing a second tube positioned along the centerline of the airway to determine outer radii of the airway by checking a 3D gradient computed along an x-axis and a y-axis of the second tube at a boundary of the second tube; and fitting the second tube to the airway by using the determined outer radii, wherein the outer radius of the tube minus the inner radius of the tube is a thickness of the airway wall.

The foregoing features are of representative embodiments and are presented to assist in understanding the invention. It should be understood that they are not intended to be considered limitations on the invention as defined by the claims, or limitations on equivalents to the claims. Therefore, this summary of features should not be considered dispositive in determining equivalents. Additional features of the invention will become apparent in the following description, from the drawings and from the claims.

DETAILED DESCRIPTION OF EXEMPLARY EMBODIMENTS

Figure 1:
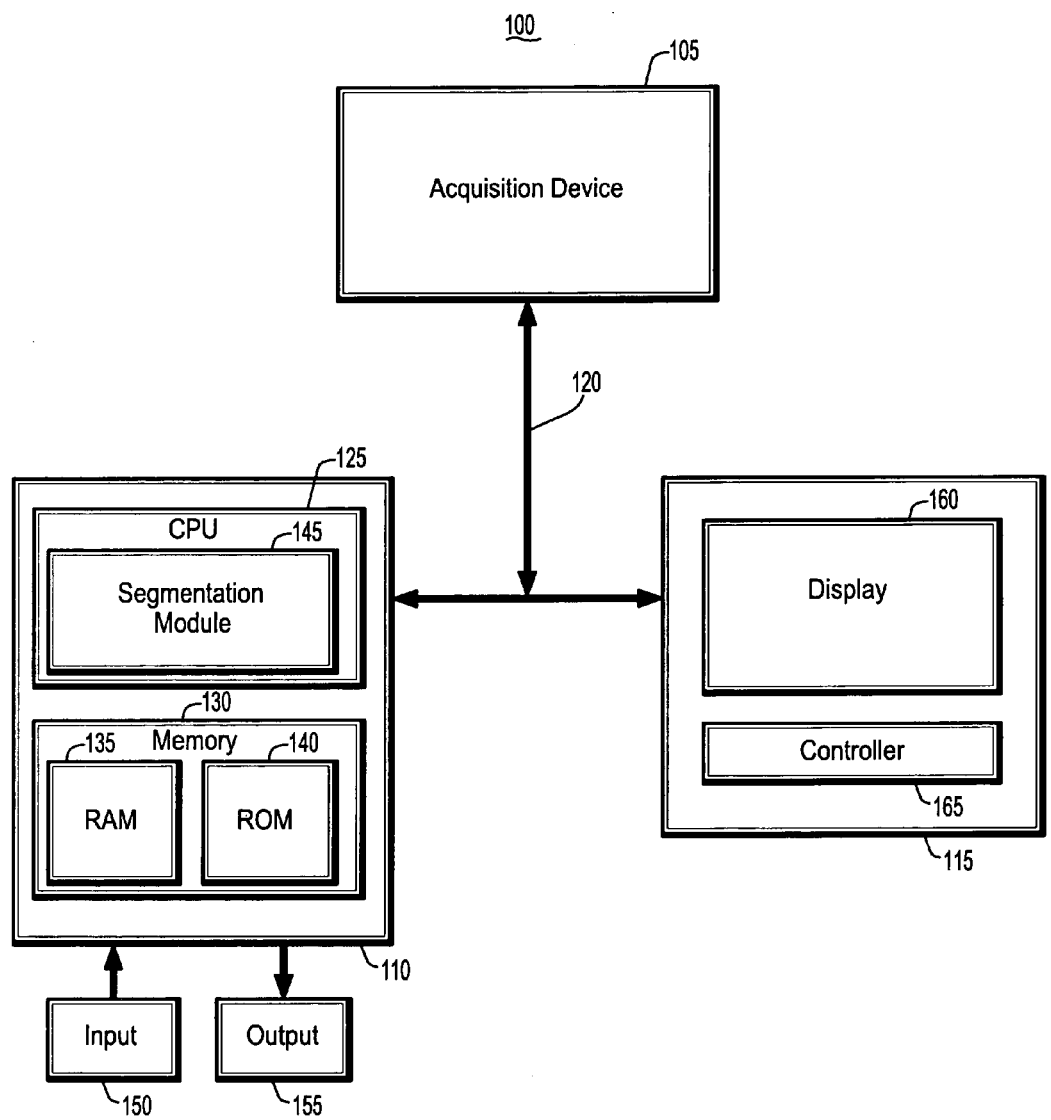
FIG. 1 is a block diagram illustrating a system for determining a size of an airway lumen and a thickness of an airway wall according to an exemplary embodiment of the present invention.

FIG. 1 is a block diagram illustrating a system 100 for determining a size of an airway lumen and a thickness of an airway wall according to an exemplary embodiment of the present invention. As shown in FIG. 1, the system 100 includes an acquisition device 105, a PC 110 and an operator's console 115 connected over a wired or wireless network 120.

The acquisition device 105 may be a multi slice computed tomography (MSCT) imaging device or any other three-dimensional (3D) high resolution imaging device such as a magnetic resonance (MR) scanner.

The PC 110, which may be a portable or laptop computer, a medical diagnostic imaging system or a picture archiving communications system (PACS) data management station, includes a CPU 125 and a memory 130 connected to an input device 150 and an output device 155. The CPU 125 includes a segmentation module 145 that includes one or more methods for determining a size of an airway lumen and a thickness of an airway wall to be discussed hereinafter with reference to FIGS. 2-6. Although shown inside the CPU 125, the segmentation module 145 can be located outside the CPU 125.

The memory 130 includes a RAM 135 and a ROM 140. The memory 130 can also include a database, disk drive, tape drive, etc., or a combination thereof. The RAM 135 functions as a data memory that stores data used during execution of a program in the CPU 125 and is used as a work area. The ROM 140 functions as a program memory for storing a program executed in the CPU 125. The input 150 is constituted by a keyboard, mouse, etc., and the output 155 is constituted by an LCD, CRT display, printer, etc.

The operation of the system 100 can be controlled from the operator's console 115, which includes a controller 165, e.g., a keyboard, and a display 160. The operator's console 115 communicates with the PC 110 and the acquisition device 105 so that image data collected by the acquisition device 105 can be rendered by the PC 110 and viewed on the display 160. It is to be understood that the PC 110 can be configured to operate and display information provided by the acquisition device 105 absent the operator's console 115, using, e.g., the input 150 and output 155 devices to execute certain tasks performed by the controller 165 and display 160.

The operator's console 115 may further include any suitable image rendering system/tool/application that can process digital image data of an acquired image dataset (or portion thereof) to generate and display images on the display 160. More specifically, the image rendering system may be an application that provides rendering and visualization of medical image data, and which executes on a general purpose or specific computer workstation. It is to be understood that the PC 110 can also include the above-mentioned image rendering system tool/application.

Figure 2:
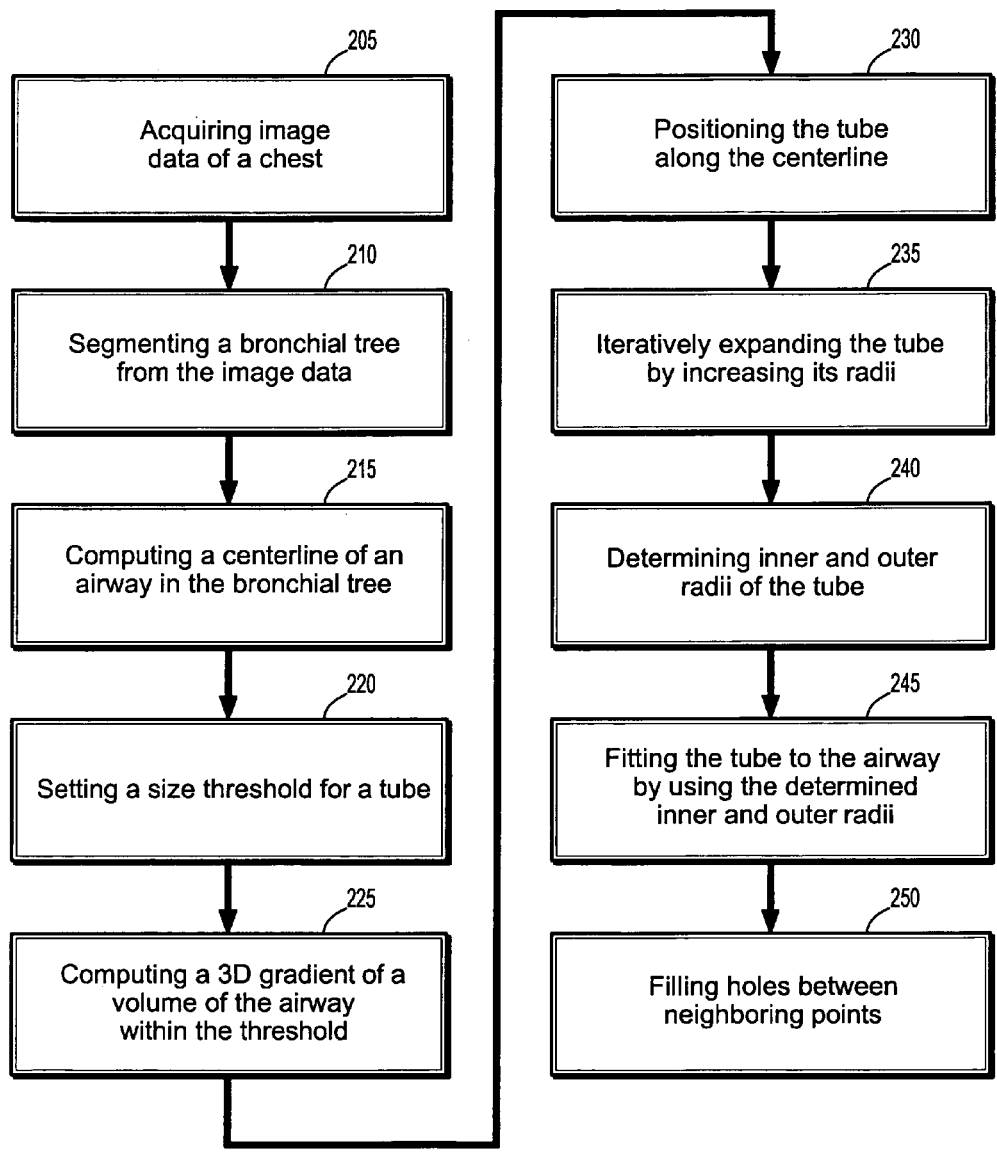
FIG. 2 is a flowchart illustrating a method for determining a size of an airway lumen and a thickness of an airway wall according to an exemplary embodiment of the present invention.

FIG. 2 is a flowchart showing an operation of a method for determining a size of an airway lumen and a thickness of an airway wall according to an exemplary embodiment of the present invention. As shown in FIG. 2, three-dimensional (3D) image data of a bronchial tree is acquired from a patient (205). This is accomplished, e.g., by using the acquisition device 105, which is operated at the operator's console 115, to scan the patient's chest thereby generating a series of 2D image slices associated with the chest. The 2D image slices are then combined to form a 3D image of the bronchial tree.

After the 3D image data of the bronchial tree is acquired, an airway in the bronchial tree is selected and the bronchial tree is segmented (210). The bronchial tree can be segmented using a number of suitable segmentation techniques. For example, the bronchial tree can be segmented by using the technique described in A P Kiraly, J P Helferty, E A Hoffman, G McLennan, W E Higgins, "Three-Dimensional Path Planning for Virtual Bronchoscopy" IEEE Transactions in Medical Imaging, pp. 1365-1379, Vol. 23, No. 11, November 2004, a copy of which is incorporated by reference herein in its entirety.

In this technique, a set of 3D airway paths are computed from multidetector computed-tomography (MDCT) images by first defining a skeleton of a segmented 3D chest image and then performing a multistage refinement of the skeleton to arrive at a final tree structure. The resulting tree structure consists of a series of paths and branch structural data suitable for quantitative airway analysis.

Once the bronchial tree has been segmented, a centerline of the selected airway is computed (215). This is accomplished, e.g., by using the tree model created from the bronchial tree segmentation described in A P Kiraly, J P Helferty, E A Hoffman, G McLennan, W E Higgins, "Three-Dimensional Path Planning for Virtual Bronchoscopy" IEEE Transactions in Medical Imaging, pp. 1365-1379, Vol. 23, No. 11, Nov. 2004. During the centerline computation, a diameter-to-background map or diameter map is created that represents highest diameter values along the tree. This map is used to provide better centering during a subsequent tree model computation. The map is also used as an initialization for a refined local segmentation of the airway.

If the tree model is not available, a region growing can be locally computed starting from a user provided click point inside the airway lumen. An upper threshold is determined iteratively depending on the size of the airway that is obtained by each segmentation. When the computed size of the airway exceeds a specific threshold, it is used as an upper limit, an active threshold is updated and the size of the airway is computed until it stabilizes. The active threshold is represented by:

$$\text{Active Threshold} = [\text{current threshold} + \text{Upper limit}]/2 \quad (1)$$

The centerline is computed by creating a distance-to-background map of this local airway segmentation. The centerline is a list of the highest distance values in the region growing result. A skeletonizaton of this segmentation can also be used to obtain the centerline. An example of this is described in A P Kiraly, J P Helferty, E A Hoffman, G McLennan, W E Higgins, "Three-Dimensional Path Planning for Virtual Bronchoscopy" IEEE Transactions in Medical Imaging, pp. 1365-1379, Vol. 23, No. 11, November 2004.

Once the centerline points are obtained, the direction from one point to another is computed. This direction determines a normal to the airway cross-section at the centerline point. This direction can be given by the tree model, by the difference between previous and next centerline point coordinates or by computing a covariance matrix of a local neighborhood of the centerline point. The size of the neighborhood can be adjusted depending on the value of the distance map at the centerline point to cover most of the region growing result. The covariance computation is given by:

$$R_{xy}(L) = \begin{cases} \frac{1}{N}\sum_{k=0}^{N-L-1}(x_{k+L}-\bar{x})(y_k-\bar{y}) & \text{For } L < 0 \\ \frac{1}{N}\sum_{k=0}^{N-L-1}(x_k-\bar{x})(y_{k+L}-\bar{y}) & \text{For } L \geq 0, \end{cases} \quad (2)$$

where L is the lag and $\bar{x}$ and $\bar{y}$ are the means of sample populations and x and y.

From the covariance matrix, eigenvectors, which correspond to the principal axes of the region around the centerline point, are computed. The three principal axes are used to extract a cross section slice at the centerline point.

Once the centerline is computed, a maximum size of a tube is set (220). This is done, e.g., by using the distance map. In the distance map, each distance value of a centerline point is the distance from the centerline point to the background of the image, with the background of the image located outside the airway By checking the distance map value for every point on the centerline, a maximum distance map value from the centerline points to the background can be obtained. It is to be understood that the size of the tube can be adjusted depending on the maximum distance map value of the centerline points along the airway.

Now that the maximum size or diameter of the tube is set, a 3D gradient of a volume of the airway within the maximum size of the tube is computed (225). This is done, e.g., by computing a 3D gradient using the gradient formula in Cartesian coordinates:

$$\nabla\phi(x,y,z) = \frac{\partial\phi}{\partial x}\hat{x} + \frac{\partial\phi}{\partial y}\hat{y} + \frac{\partial\phi}{\partial z}\hat{z}, \quad (3)$$

with x, y and z being the principal axes.

The gradient computation is performed along the axes of the tube, not along the axes of the original volume. The gradient is computed using original data or reformatted data. For accuracy, data that has been reformatted using a linear interpolation is used. This allows more precise information regarding inner and outer borders of the airway.

Figure 3:
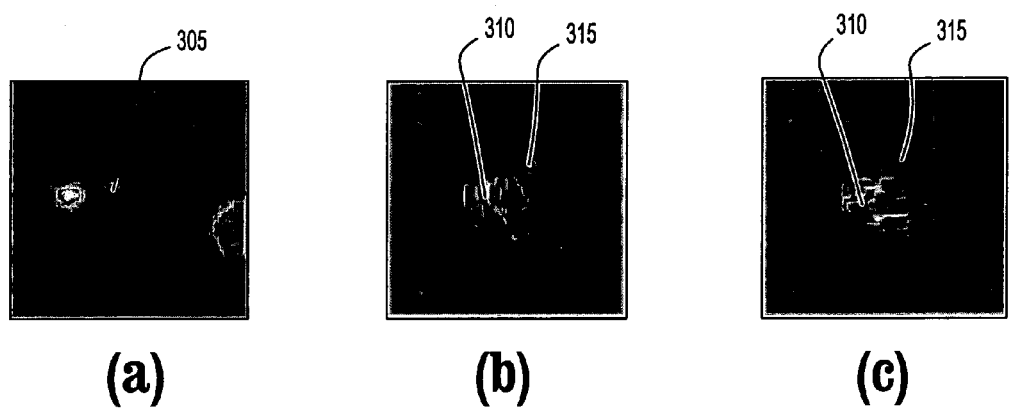
FIG. 3 is a set of images illustrating a gradient computation according to an exemplary embodiment of the present invention.

By using reformatted data, inner and outer borders of an airway can be observed. For example, as shown in FIG. 3, inner and outer borders 310 and 315 of an airway 305 (identified by a faint white circle in the center of image (a)), can be viewed as shown in images (b) and (c). In FIG. 3, image (a) illustrates a cross-section of the airway 305 and images (b) and (c) illustrate the cross-section of a 3D gradient computed along the x and y directions within the tube, respectively.

Now that the centerline points along the airway and an estimated diameter of the airway lumen are known, the tube is positioned along the centerline (230). This is done, e.g., by placing center points of the tube at centerline locations. Inner tube computations are performed first followed by outer tube computations. Using either a global or local background-to-diameter map, the initial tube sizes are set. It is to be understood that only a central part of the airway, e.g., the central two thirds, will be segmented to avoid a bifurcation in the airway.

With the tube positioned along the centerline, the tube is grown or expanded by iteratively increasing its radii (235). For example, starting from radii=zero, the tube is expanded by a quarter of an isotropic voxel. At each iteration, the gradients are checked at the boundary of the tube. For example, at each iteration, the cross-section of the tube is stored in the memory 130 of the PC 110. This enables inner and outer radii that fit the airway's lumen and wall shapes to be determined (240).

When the tube is grown, it is separated into four sections. For example, right and left sections for the gradient computed in the x direction and top and bottom sections for the gradient computed in the y direction. The sum of each circle half for each value of the radius is monitored. The mean gradient value for each of the four sections is computed by using the four mean gradient values at the boundaries of the respective sections at each iteration of the increasing radii. It is to be understood that the use of circle halves reduces a partial volumes effect since the curves are computed using the gradients of the x and y directions. This increases the chances of finding a missing or discontinued boundary since a region targeted by the half circles is larger than a region concerned with partial volume effects.

Figure 4:
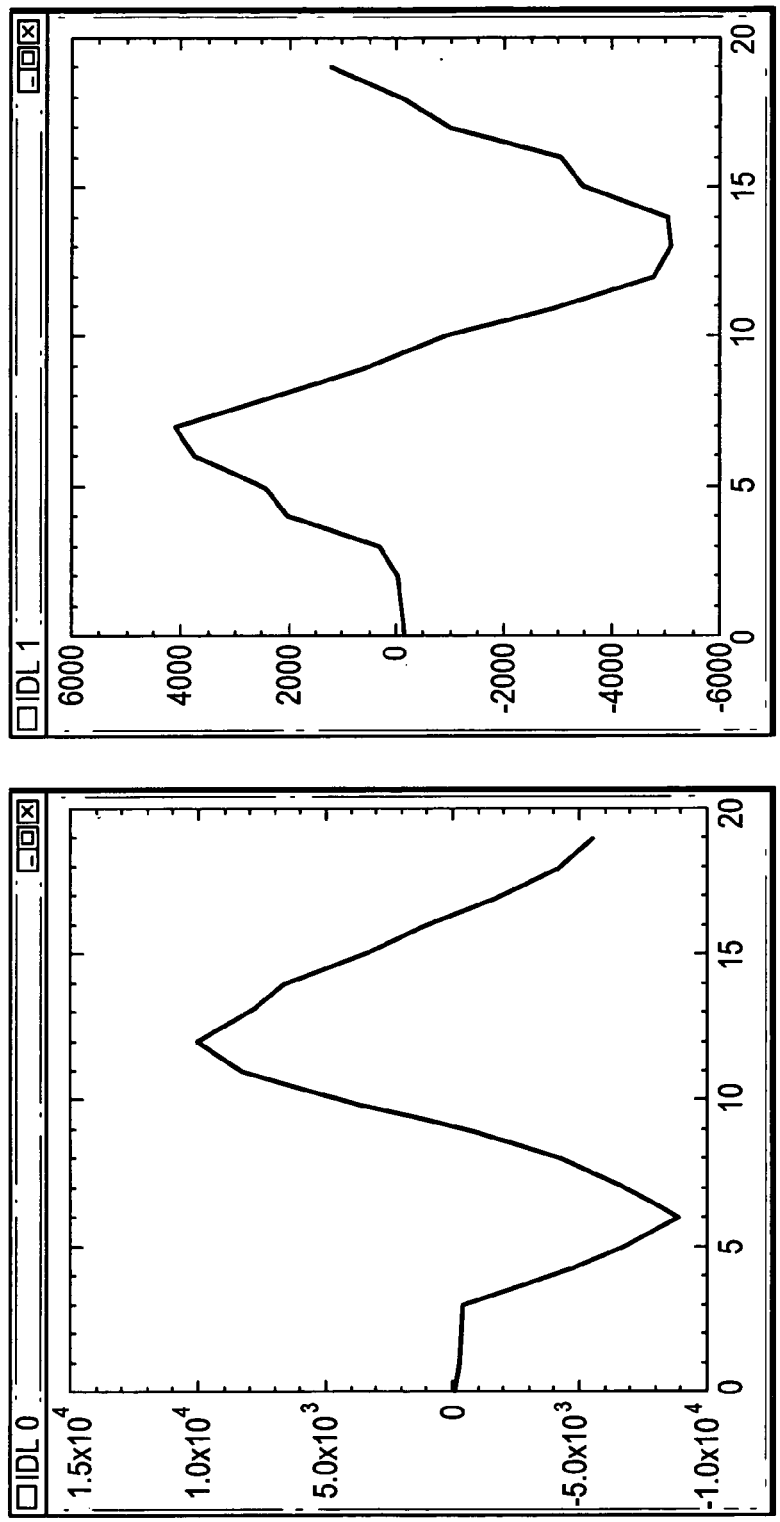
FIG. 4 is a pair of graphs illustrating a gradient sum of circle parts as a function of circle radius according to an exemplary embodiment of the present invention.

By plotting the gradient sum along the circle halves as a function of radius as shown by the graphs in FIG. 4, a peak analysis enables the inner and outer diameters of the tube in the right, left, bottom and top directions to be determined. For example, in FIG. 4, graph (a) illustrates the gradient sum of the circle parts as a function of radius along the x direction and graph (b) illustrates the gradient sum of the circle parts as a function of radius along the y direction. In FIG. 4, minimum and maximum peaks of these graphs correspond to the inner and outer radii of the tube, respectively, that best fit the airway.

Figure 5A:
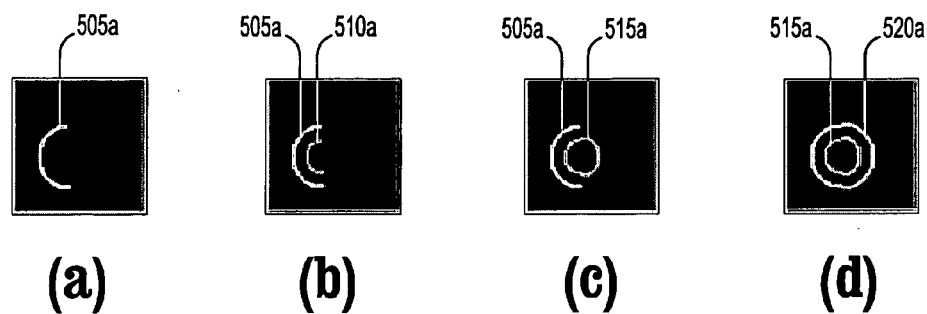
FIG. 5A is a set of images illustrating optimized inner and outer circle radii based on gradient information curves computed in FIG. 4 along an x direction according to an exemplary embodiment of the present invention.
Figure 5B:
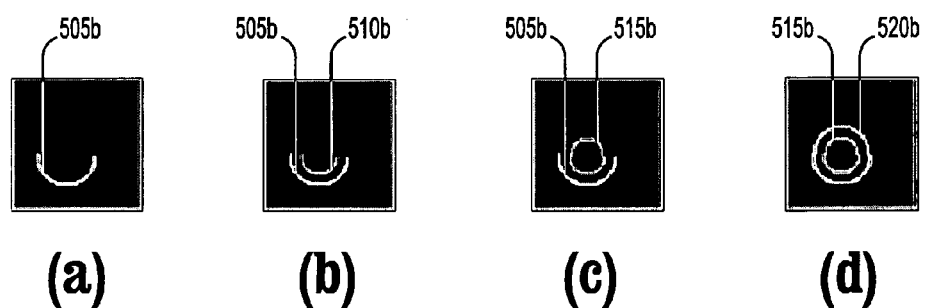
FIG. 5B is a set of images illustrating optimized inner and outer circle radii based on gradient information curves computed in FIG. 4 along a y direction according to an exemplary embodiment of the present invention.

FIGS. 5A and 5B illustrate optimized inner and outer tube diameters found within the gradient information curves along the x and y directions, respectively. In FIGS. 5A and 5B, curves 505a,b of image (a) illustrate a first half outer radius of the tube, curves 510a,b of image (b) illustrate a first half inner diameter of the tube, curves 515a,b of image (c) illustrate a last half inner diameter of the tube thereby completing the full inner diameter and curves 520a,b of image (d) illustrate a last half outer diameter of the tube thereby completing the full outer diameter. More specifically, the inner diameters represent the luminal area of the airway and the outer diameters represent the airway wall. The inner and outer radii are given by two full curves from FIG. 5A and two full curves from FIG. 5B, 510a,b, 515a,b and 505a,b, 520a,b, respectively.

By using half circles as shown in FIGS. 5A and 5B, it can be determined if correct radii have been found. For example, when there is a partial volume effect, if one half curve gives a radius outside the airway, the corresponding radius can be recovered by modifying the half curve to better match the other curves.

The segmentation of the airway is adjusted by using the selected inner and outer diameters (245). In other words, the tube is fit to the airway by using the determined inner and outer radii. This is done, e.g., by validating points from the gradients along the x and y directions that are common to the inner and outer diameters as part of the segmentation. In most cases, both boundaries have common points that are confirmed as part of the airway wall or lumen diameter.

For the rest of the points, e.g., for points that are only part of diameters of the gradient along the x direction or the gradient along the y direction but not both, a threshold corresponding to a third of the maximum value of the x and y gradients is computed. For each of the points below the threshold, corresponding gradient values at the same location are checked and if the value is greater than the threshold value, the point is kept otherwise it is discarded.

Since this process is done separately for the inner and outer diameters, it can leave discontinuities or holes along delineations of the inner and outer diameters. To fix this, the discontinuities or holes are filled (250). This is done, e.g., by taking farthest points from the centerline and filling the holes between the neighboring points.

Figure 6:
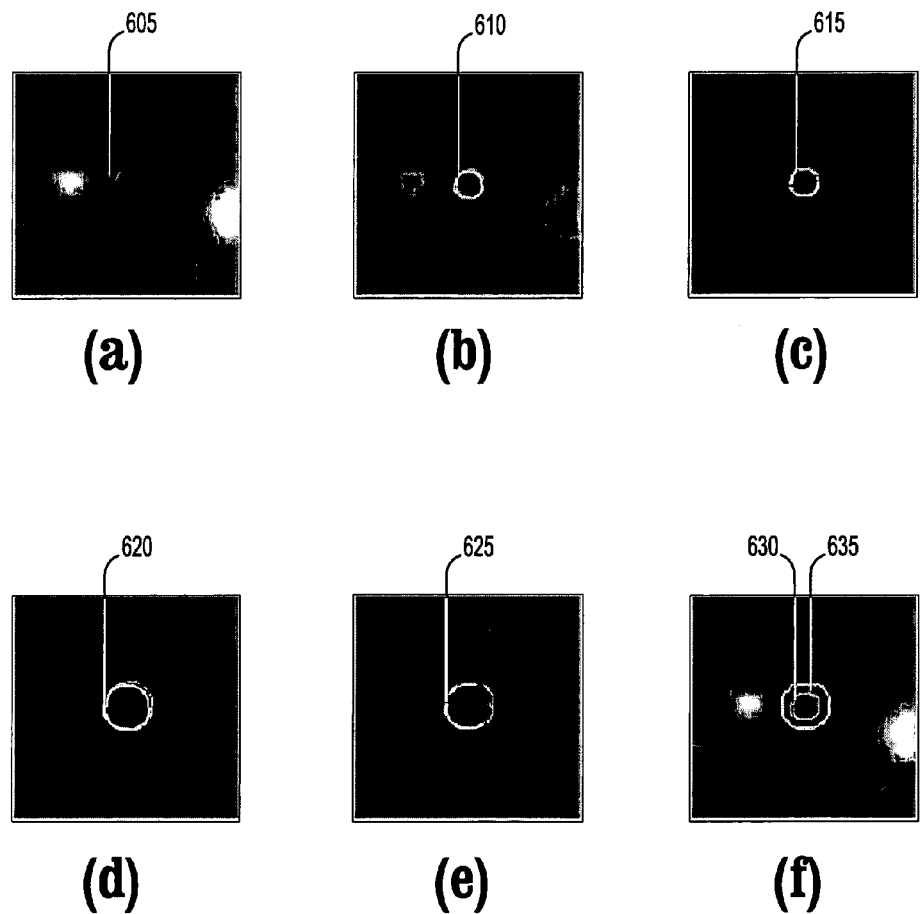
FIG. 6 is a sequence of images illustrating a method for determining a size of an airway lumen and a thickness of an airway wall according to an exemplary embodiment of the present invention.

FIG. 6 is a sequence of images illustrating a method for segmenting an airway lumen and wall according to an exemplary embodiment of the present invention. Image (a) illustrates an original cross-section of an airway 605, which is identified by a faint white circle in the center of the image that is to be segmented. Image (b) illustrates a lumen of the airway, where the lumen is segmented using the x and y gradients. In this image, inner and outer diameter halves 610 from the x and y gradients are merged. Image (c) illustrates the lumen segmented after refining the gradient. The merged inner diameter halves 615 of image (b) are pruned (e.g., they undergo thresolding, gradient comparison and verification). Image (d) illustrates the segmentation of a wall of the airway using the x and y gradients. In this image, merged outer diameter circle halves 620 are shown. Image (e) illustrates wall segmentation after pruning. The merged outer diameter circle halves 620 are pruned. Image (f) illustrates the final segmentation of images (b-e) after hole filling. Inner and outer diameters 630 and 635 of the airway are shown in the center of image (f).

Since a tube is used for segmentation, this limits the diameter differences that may be present along the airway. To compensate for this, a tolerance regarding a difference from the diameter map of the airway is set to introduce a smoothness to the deformation of the tube resulting from the gradient process. For the inner tube, the tolerance can be defined as $Tol_i = 5\% * diam_i$ with $diam_i$ being the diameter found by the diameter map and "i" being the index of a corresponding centerline point. The tolerance could also be expressed by using the highest diameter along the airway diameter map: $Tol=5\%*max(diam_i)$. The tolerance is positive and the minimum diameter is the minimum from the diameter map. For the outer tube, a median filter on the radii can be used to remove any large radii.

In accordance with an exemplary embodiment of the present invention, the walls of an airway are automatically segmented by using dual tubes, wherein a thickness of the wall is determined by a difference between the two tubes. The use of the tubes reduces an over-segmentation generally caused by the partial volume effect. Further, where a 2D segmentation algorithm does not detect any wall boundaries, the tubes are capable of adjusting and compensating for any missing boundaries. In addition, if a bronchial tree is not available, the dual tube segmentation technique uses a region growing algorithm to estimate a size of an airway to be segmented. Moreover, the technique is accurate and consistent since it uses a quarter voxel trilinear interpolation to estimate the gradient. The interpolation is done directly on the original volume and not on a volume of interest around the airway. Therefore, it is not user click dependent.

It is to be understood that the present invention may be implemented in various forms of hardware, software, firmware, special purpose processors, or a combination thereof. In one embodiment, the present invention may be implemented in software as an application program tangibly embodied on a program storage device (e.g., magnetic floppy disk, RAM, CD ROM, DVD, ROM, and flash memory). The application program may be uploaded to, and executed by, a machine comprising any suitable architecture.

It is to be further understood that because some of the constituent system components and method steps depicted in the accompanying figures may be implemented in software, the actual connections between the system components (or the process steps) may differ depending on the manner in which the present invention is programmed. Given the teachings of the present invention provided herein, one of ordinary skill in the art will be able to contemplate these and similar implementations or configurations of the present invention.

It should also be understood that the above description is only representative of illustrative embodiments. For the convenience of the reader, the above description has focused on a representative sample of possible embodiments, a sample that is illustrative of the principles of the invention. The description has not attempted to exhaustively enumerate all possible variations. That alternative embodiments may not have been presented for a specific portion of the invention, or that further undescribed alternatives may be available for a portion, is not to be considered a disclaimer of those alternate embodiments. Other applications and embodiments can be implemented without departing from the spirit and scope of the present invention.

It is therefore intended, that the invention not be limited to the specifically described embodiments, because numerous permutations and combinations of the above and implementations involving non-inventive substitutions for the above can be created, but the invention is to be defined in accordance with the claims that follow. It can be appreciated that many of those undescribed embodiments are within the literal scope of the following claims, and that others are equivalent.

What is claimed is:

1. A method for determining a size of an airway lumen and a thickness of an airway wall, comprising:
    computing a centerline of an airway;
    computing a three-dimensional (3D) gradient of a volume of the airway within a first threshold;
    positioning a tube along the centerline;
    iteratively expanding the tube by increasing its radius until the radius of the tube reaches the first threshold;
    determining inner and outer radii of the tube by checking the 3D gradient computed along an x-axis and a y-axis of the tube at a boundary of the tube at each iteration; and
    fitting the tube to the airway by using the determined inner and outer radii,
    wherein the inner radius of the fit tube is half an inner diameter of the airway lumen and the outer radius of the fit tube minus the inner radius of the fit tube is a thickness of the airway wall, and an outer diameter of the airway is equal to two times the outer radius;
    wherein fitting the tube to the airway by using the determined inner and outer radii comprises:
    validating, as part of the airway, points from the inner and outer diameters that are common to the 3D gradients computed along the x and y-axes of the tube;
    computing a second threshold corresponding to a third of a maximum value of the 3D gradients computed along the x and y-axes of the tube for inner and outer diameter points from only one of the 3D gradients computed along the x and y-axes of the tube;
    discarding points from only one of the 3D gradients computed along the x and y-axes of the tube when they are below the second threshold; and
    validating points from only one of the 3D gradients computed along the x and y-axes of the tube when they are above the second threshold.

2. The method of claim 1, wherein the first threshold is a maximum size of the tube.

3. The method of claim 1, further comprising:
    increasing the radius of the tube by a quarter of an isotropic voxel at each iteration.

4. The method of claim 1, further comprising:
    separating the tube into right and left sections for the 3D gradient computed along the x-axis of the tube and into top and bottom sections for the 3D gradient computed along the y-axis of the tube.

5. The method of claim 4, wherein determining inner and outer radii of the tube comprises:
    computing a mean gradient curve of the right, left, top and bottom sections; and
    performing a peak analysis of the mean gradient curves.

6. The method of claim 5 wherein a maxim maximum peak of the mean gradient curves corresponds to an inner radius of the tube and a minimum peak of the mean gradient curves corresponds to an outer radius of the tube.

7. The method of claim 1, further comprising:
    filling holes between neighboring points that have been validated in the fit airway by placing farthest distance value points from the centerline between the neighboring points.

8. The method of claim 1, further comprising:
    acquiring an image of a chest including the airway by using computed tomography or magnetic resonance imaging.

9. The method of claim 1, wherein the airway is a trachea or a bronchi.

10. A system for determining a size of an airway lumen and a thickness of an airway wall, comprising:
    a memory device for storing a program;
    a processor in communication with the memory device, the processor operative with the program to:
    compute a centerline of an airway;
    compute a three-dimensional (3D) gradient of a volume of the airway within a first threshold;
    position a tube along the centerline;
    iteratively expand the tube by increasing its radius until the radius of the tube reaches the first threshold;
    determine inner and outer radii of the tube by checking the 3D gradient computed along an x-axis and a y-axis of the tube at a boundary of the tube at each iteration; and
    fit the tube to the airway by using the determined inner and outer radii,
    wherein the inner radius of the fit tube is half an inner diameter of the airway lumen and the outer radius of the fit tube minus the inner radius of the fit tube is a thickness of the airway wall, and an outer diameter of the airway is equal to two times the outer radius;
    wherein when fitting the tube to the airway by using the determined inner and outer radii the processor is further operative with the program to:
    validate, as part of the airway, points from the inner and outer diameters that are common to the 3D gradients computed along the x and y-axes of the tube;
    compute a second threshold corresponding to a third of a maximum value of the 3D gradients computed along the x and y-axes of the tube for inner and outer diameter points from only one of the 3D gradients computed along the x and y-axes of the tube;
    discard points from only one of the 3D gradients computed along the x and y-axes of the tube when they are below the second threshold; and validate points from only one of the 3D gradients computed along the x and y-axes of the tube when they are above the second threshold.

11. The system of claim 10, wherein the first threshold is a maximum size of the tube.

12. The system of claim 10, wherein the processor is further operative with the program to:
increase the radius of the tube by a quarter of an isotropic voxel at each iteration.

13. The system of claim 10, wherein the processor is further operative with the program to:
separate the tube into right and left sections for the 3D gradient computed along the x-axis of the tube and into top and bottom sections for the 3D gradient computed along the y-axis of the tube.

14. The system of claim 13, wherein when determining inner and outer radii of the tube the processor is further operative with the program to:
compute a mean gradient curve of the right, left, top and bottom sections; and perform a peak analysis of the mean gradient curves.

15. The system of claim 14, wherein a maximum peak of the mean gradient curves corresponds to an inner radius of the tube and a minimum peak of the mean gradient curves corresponds to an outer radius of the tube.

16. The system of claim 10, wherein the processor is further operative with the program to:
fill holes between neighboring points that have been validated in the fit airway by placing farthest distance value points from the centerline between the neighboring points.

17. The system of claim 10, wherein the processor is further operative with the program to:
acquire an image of a chest including the airway by using a computed tomography or magnetic resonance imaging device.

18. The system of claim 10, wherein the airway is a trachea or a bronchi.

* * * * *